(12) United States Patent
Kudlu

(10) Patent No.: US 7,971,761 B1
(45) Date of Patent: Jul. 5, 2011

(54) APPARATUS AND METHOD FOR NASAL PASSAGE RINSE

(76) Inventor: Narasimha Kudlu, Concord, CA (US)

( * ) Notice: Subject to any disclaimer, the term of this patent is extended or adjusted under 35 U.S.C. 154(b) by 714 days.

(21) Appl. No.: 11/584,696

(22) Filed: Oct. 20, 2006

(51) Int. Cl.
*B67D 3/00* (2006.01)

(52) U.S. Cl. .................................................... 222/481.5

(58) Field of Classification Search ............... 604/19
See application file for complete search history.

(56) References Cited

U.S. PATENT DOCUMENTS

| | | | |
|---|---|---|---|
| 3,847,145 A | 11/1974 | Grossan | |
| 4,513,891 A | 4/1985 | Hain | |
| 4,925,128 A | 5/1990 | Brody | |
| 5,806,723 A * | 9/1998 | DuBose | 222/211 |
| 5,899,878 A | 5/1999 | Glassman | |
| 6,293,436 B2 | 9/2001 | Faughnder | |
| 6,361,521 B1 * | 3/2002 | Erickson | 604/37 |
| 6,540,718 B1 * | 4/2003 | Wennek | 604/94.01 |
| 6,669,059 B2 | 12/2003 | Mehta | |
| 6,688,497 B2 | 2/2004 | Mehta | |
| 6,736,792 B1 * | 5/2004 | Liu | 604/94.01 |

* cited by examiner

*Primary Examiner* — Nicholas D Lucchesi
*Assistant Examiner* — Jason Flick
(74) *Attorney, Agent, or Firm* — John E. Bargero

(57) ABSTRACT

An apparatus and method for preparing saline solution and using the saline solution for rinsing nasal passages. The apparatus includes a container (10) having sidewalls and opening for a removable cap (13). The cap has an external tapering hollow nozzle (14). The nozzle (14) is inserted into one end of a flexible tube (21). The other end of the tube (21) is inserted into a hollow removable contoured dispenser tip (23) which is shaped to fit a human nostril comfortably. A thin tubular conduit (19) is attached to the cap by means of a fitting (16) and the conduit extends into the container (10) close to its bottom when the apparatus is fully assembled. A saline solution is prepared by adding iodine free common salt to warm distilled or boiled water in the container. After attaching the cap (13) to the container (10) and inserting the dispenser tip (23) into one nostril, a user bends forward and tilts the head to the side of the other nostril and breaths through open mouth. The user then allows the saline solution to flow by gravity through one nostril and come out through the other open nostril, after passing through nasal passages, by holding the container (10) inverted (bottom up cap down) and raising it above the level of nostrils. The rate of flow of the saline solution to the nostril can be controlled by varying the height at which the container is held above the level of nostrils.

8 Claims, 3 Drawing Sheets

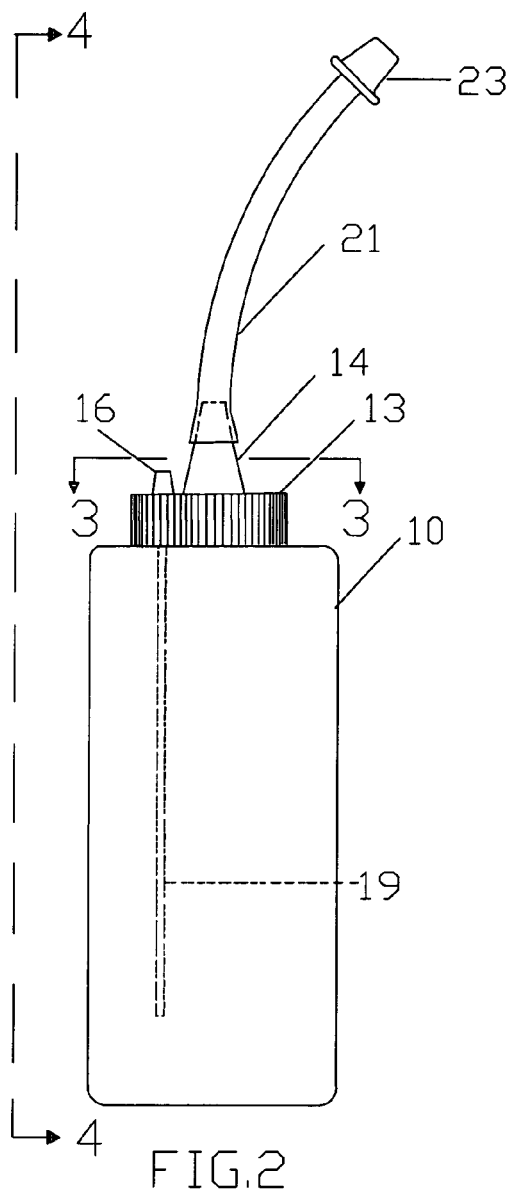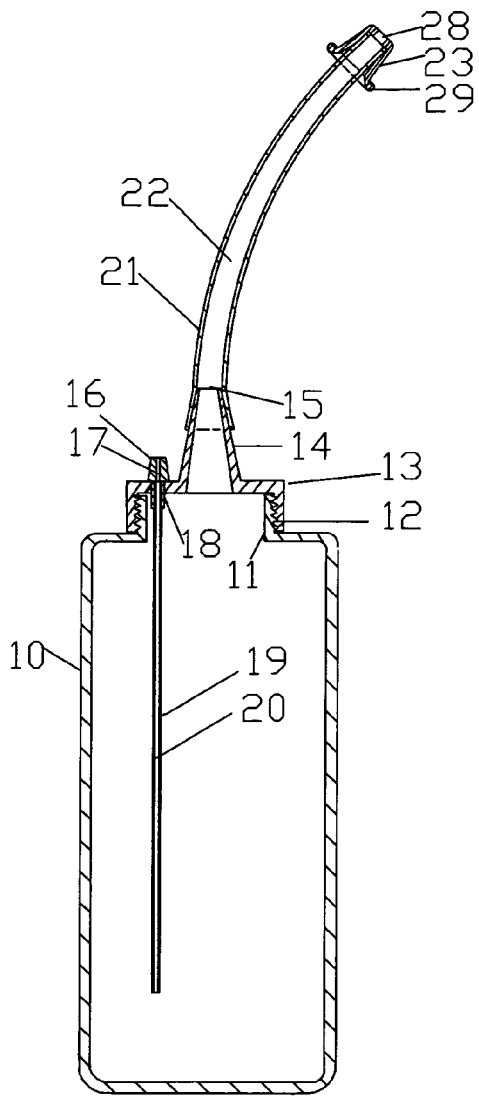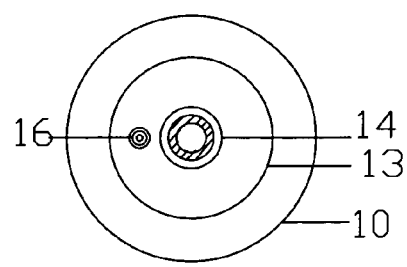

APPARATUS AND METHOD FOR NASAL PASSAGE RINSE

CROSS-REFERENCE TO RELATED APPLICATIONS

Not Applicable

FEDERALLY SPONSORED RESEARCH

Not Applicable

SEQUENCE LISTING OR PROGRAM

Not Applicable

BACKGROUND OF THE INVENTION

1. Field of Invention

This invention relates to apparatus and methods for rinsing nasal passages with saline solution.

2. Background of the Invention

Allergens are organic particles that attach to the nasal mucosa or respiratory mucosa and lead to the development of an antibody which creates a series of chemical reactions leading to symptoms. Allergies to various allergens can cause rhinitis and sinusitis. It is known that an effective nasal rinse can significantly reduce or permanently cure the symptoms of nasal allergies and sinus disease.

Conventional nasal rinsing equipment can be crude and many find it unsuitable for use. Currently various types of dispensers that can inject saline solution into user's nasal passage are available. U.S. Pat. No. 3,847,145 to Grossan (1974) discloses a nasal irrigation system which receives fluid from a fluid source, typically in a pulsating mode under pressure, and transfers this fluid through a hose to an applicator, through which fluid enters the nostril. The applicator is uncomfortable to use for the user must position their fingers on a small finger grip. Additionally, the applicator lacks any structure thereon from which the user can control fluid flow. U.S. Pat. No. 5,899,878 to Glassman (1999) discloses a nasal irrigation system which also receives a pressurized stream of fluid from a fluid source. U.S. Pat. No. 6,669,059 to Mehta (2003) discloses a nasal irrigation system in which the container of saline solution is squeezed to force the saline solution to the nasal passages.

All the nasal rinsing equipment currently available suffer from a number of disadvantages:

(a) saline solution is dispensed to the nostrils by force either by squeezing a flexible fluid container or by using a pressurized fluid source or by using syringes.
(b) fluid flow is not continuous through the nasal passages resulting in uncomfortable sensation.
(c) the saline solution from the nostril along with mucus is sucked back into the container when squeezing of the container is stopped and the pressure is released.
(d) it is hard to inject the entire content of the container into the nostril by squeezing the container as some of it is retained at the bottom of the container.
(e) for proper use, the dispensing tip should comfortably fit into user's nostril. Equipment having a dispenser tip designed for a certain size nostril can be useless for someone with smaller or larger nostrils. Improperly designed dispenser tips can cause the saline solution to be dispensed into the nasal passage without sufficiently dispersing before reaching the back of the nasal passage, resulting in an uncomfortable or painful sensation for the user. Thus, there is a need for equipment having dispenser tips that fit comfortably in human nostrils of varying sizes.

For the foregoing reasons, there is a need for a method and an apparatus for preparing and dispensing a saline solution that is simple to make, simple to use, portable, suitable for use by persons having nostrils of different sizes, capable of rinsing nasal passages with a steady stream of liquid without pressurizing the saline solution or using pressure to dispense liquid to the nostrils, precludes the possibility of backflow of solution from the nostrils to the container and uses the solution completely from the container.

SUMMARY

The present invention is an improvement over prior techniques for such rinsing, and contemplates the application to a person's nostril, while the head is generally inclined to one side, face down, of a steady flow of warm saline water solution. It provides an apparatus and a method for rinsing nasal passages with saline solutions. The apparatus includes a removable cap and a container for preparing and holding saline solution. The cap and the container are connected together with a liquid tight joint. A saline solution is prepared by adding iodine free common salt to warm distilled or boiled water in the container. The cap has a cylindrical lower portion and a flat upper portion with a centrally located hollow nozzle and a small hole adjacent to the nozzle for attaching a fitting which holds a thin tubular conduit. One end of a flexible tube is attached to the nozzle on the cap and other end is attached to a removable hollow contoured dispenser tip which fits human nostrils. A thin tubular conduit is attached to the cap by means of a fitting to allow air to flow into the container during nasal rinsing. After closing the container with the cap and inserting the dispenser tip into one nostril, a user bends forward and tilts the head to the side of the other nostril and breaths through open mouth. The user then allows the saline solution to flow by gravity through one nostril and come out through the other open nostril, after passing through nasal passages, by holding the container inverted and raising it above the level of nostrils. The rate of flow of the saline solution to the nostril can be controlled by varying the height at which the container is held above the level of the nostrils. The flow of the solution to the nostril can be instantly stopped, if needed, either by lowering the container below the level of the nostrils or by blocking air flow to the container with a finger tip placed on the fitting.

The advantages of the present invention:

(a) This invention can be used by children and adults for nasal rinse with a steady stream of saline solution without injecting or applying pressure.
(b) The rate of flow of the solution to the nostrils can be easily controlled by raising or lowering the container above the level of nostrils.
(c) The flow of saline solution from the container can be stopped instantly by lowering the container below the level of nostrils or by blocking air to the container by placing a finger tip on the fitting.
(d) The apparatus includes multiple removable dispenser tips to comfortably fit large, regular and small size nostrils.
(e) There is no possibility of backflow of solution from the nostrils into the container.
(f) Entire solution in the container can be applied to the nostril without leaving any residual solution at the bottom of the container.
(g) The user can inspect all parts of the apparatus to ensure cleanliness. It can be easily sterilized with boiling water.

(h) It is simple to make, simple to use, simple to clean and inexpensive to replace.
(i) The flexible tube with the dispenser tip can be removed from the cap and stored in the container thus making it convenient to carry during travels.

DESCRIPTION OF DRAWINGS OF THE PREFERRED EMBODIMENT

FIG. 2 shows a front view of the dispenser assembly.

FIG. 3 shows a top view of the dispenser assembly as seen at level 3-3 in FIG. 2.

FIG. 4 shows a cross-sectional view of the dispenser assembly, section 4-4 shown on FIG. 2.

DRAWINGS

Reference Numerals

| 10 | container | 11 | neck |
| 12 | threads | 13 | cap |
| 14 | nozzle | 15 | tip of the nozzle |
| 16 | fitting | 17 | bore of the fitting |
| 18 | tubular extension | 19 | tubular conduit |
| 20 | bore of the tubular conduit | 21 | flexible tube |
| 22 | conduit | 23 | dispenser tip |
| 24 | upper part | 25 | base |
| 26 | sloping surface | 27 | rounded outer edges |
| 28 | opening | 29 | lip |

DETAILED DESCRIPTION OF THE PREFERRED EMBODIMENT

Figure 1:
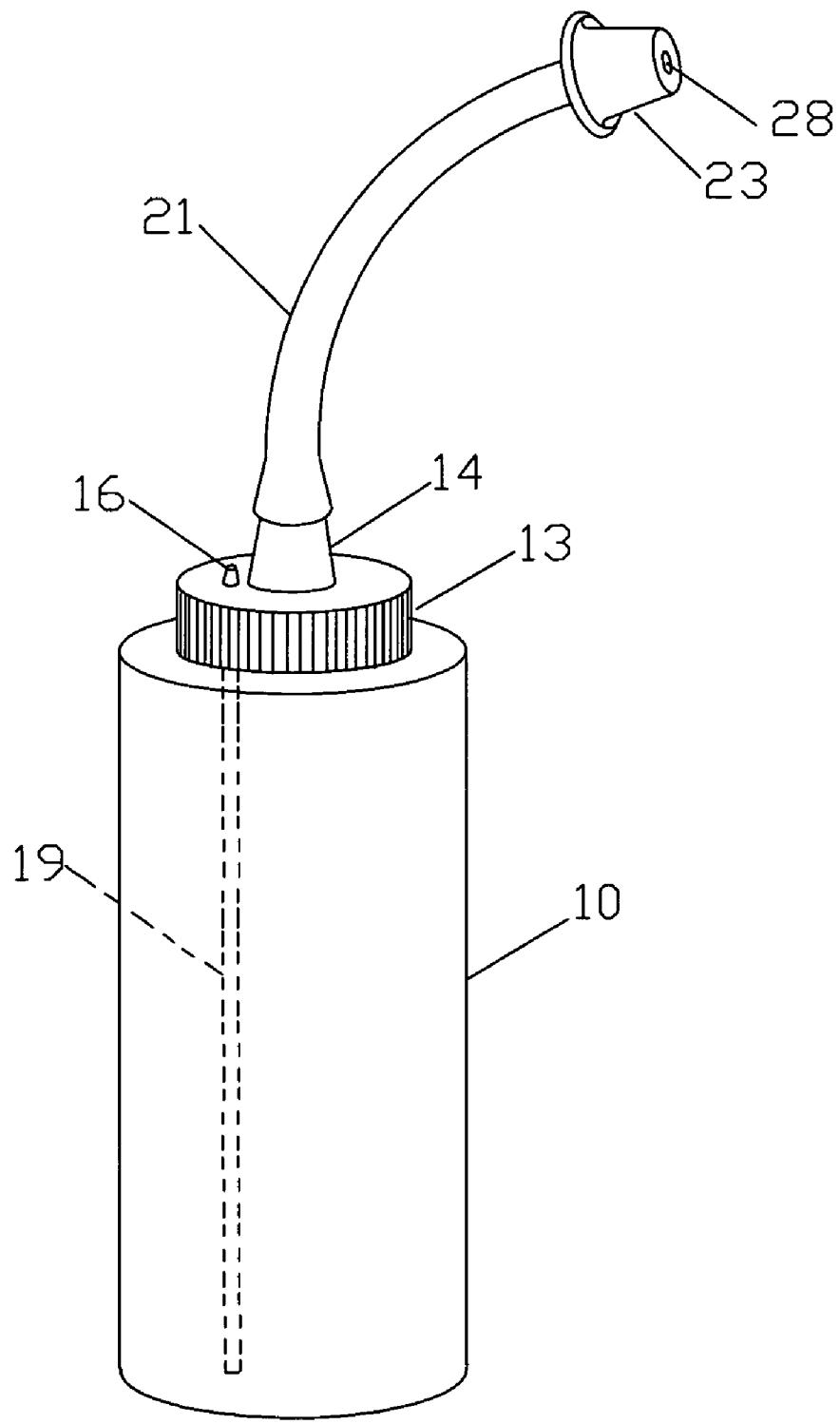
FIG. 1 shows a 3 dimensional view of a dispenser assembly.
Figure 5:
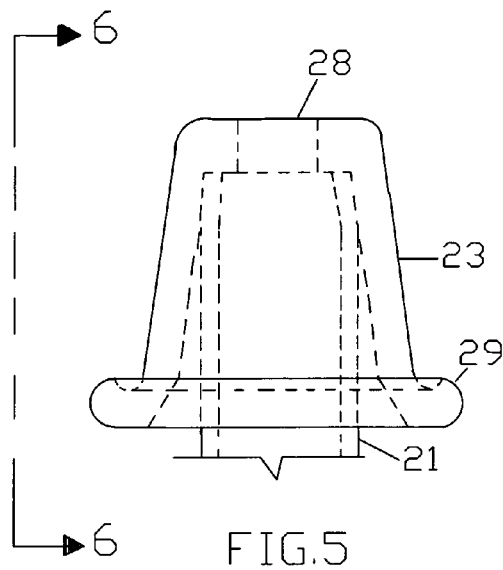
FIG. 5 shows an enlarged front view of the dispenser tip.
Figure 6:
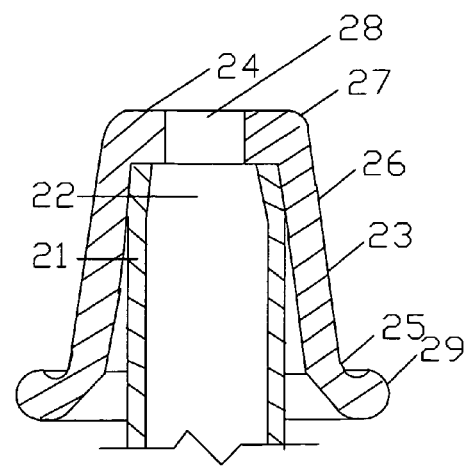
FIG. 6 shows an enlarged cross-sectional view of the dispenser tip and the flexible tube assembly, section 6-6 shown on FIG. 5.
Figure 7:
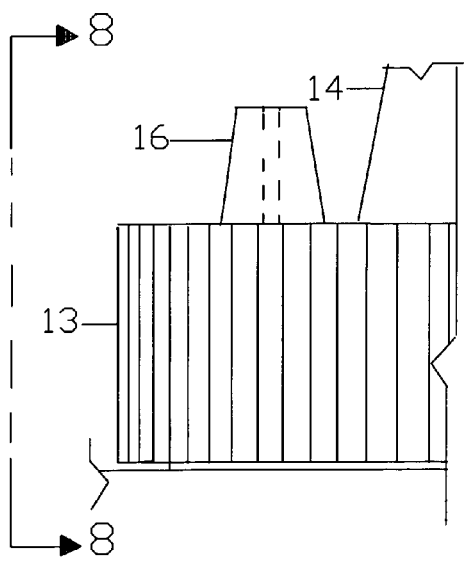
FIG. 7 shows an enlarged front view of the fitting on the cap.
Figure 8:
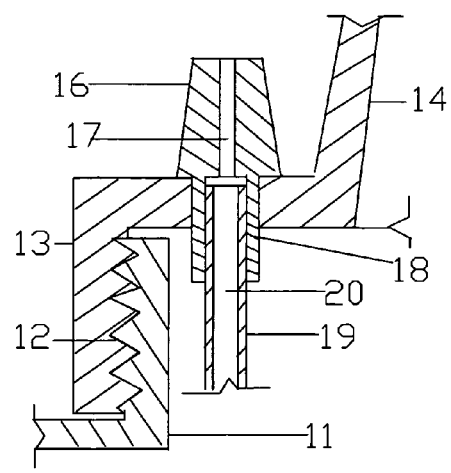
FIG. 8 shows an enlarged cross-sectional view of the fitting on the cap with the tubular conduit, section 8-8 shown on FIG. 7

FIG. 1 shows an apparatus for using saline solution to rinse nasal passages. The apparatus includes a container 10, a cap 13 having a hollow nozzle 14 and a fitting 16 for attaching a thin tubular conduit 19 to the cap 13. The tip of the hollow nozzle 14 is inserted into one end of a flexible tube 21. The other end of the tube 21 is inserted into a hollow contoured dispenser tip 23 which has a central opening 28. The fitting 16, which is inserted into a small hole in the cap 13, attaches the thin tubular conduit 19. The thin tubular conduit 19 extends into the container 10 close to its bottom. The cap 13 can be removed from the container 10 by rotating the cap 13 counter clockwise to allow the container 10 to be filled with saline solution.

Referring to FIG. 2 through FIG. 8, the apparatus will be described in greater detail. The container 10, can be constructed from any nontoxic materials, has cylindrical shape and is provided with a top opening with a neck 11 that can include threads 12 to provide tight connection to the cap 13. The cap 13 can be connected to the container 10 in other convenient ways. The container 10 can hold at least 12 ounces of liquid. The container 10 can be of other shapes and sizes.

The exterior of the cap 13 has a cylindrically shaped lower portion and a flat upper portion with a centrally located tapering hollow nozzle 14 and a small round hole located close to the nozzle 14 for inserting a hollow fitting 16 which attaches a thin tubular conduit 19 to the cap 13. The cylindrically shaped lower portion of the cap 13 is provided with threads to secure the cap onto the container 10. The cap 13 can be constructed from any non toxic material. Cap 13 can be of other shapes and sizes and without threads.

The flexible tube 21, can be constructed from any nontoxic material, is hollow and serves as a conduit 22 to transport liquid from the container 10 to the opening 28 of the dispenser tip 23. The tip 15 of the hollow tapering nozzle 14 is inserted into one end of the flexible tube 21 and the other end of the flexible tube 21 is inserted into a hollow contoured dispenser tip 23 which has a central opening 28. The external diameter of the flexible tube 21 is about 9 mm and diameter of the conduit 22 is about 6 mm. The length is less than 160 mm. The flexible tube 21 can have different lengths and diameters.

The dispenser tip 23 can be constructed from any nontoxic material, has a hollow body, has an upper part 24 with rounded outer edges 27 and a centrally located round opening 28, has a sloping surface 26 from the upper part 24 to the base 25 and has a lip 29 which protrudes away from the sloping surface 26. Regular size dispenser tip 23 has an upper part 24 with external diameter of about 13 mm, the base 25 with an external diameter of about 16 mm, the lip 29 with an external diameter of about 25 mm and the distance between the base and the upper part 24 is about 15 mm. The diameter of the opening 28 is about 6 mm. A separate dispenser tip, with an upper part having an external diameter as low as 9 mm, can be constructed if required for use by children without altering other overall dimensions.

The thin tubular conduit 19, can be constructed from any nontoxic flexible material, has small central bore 20 to serve as a conduit for air to enter the container 10 during nasal rinsing. The thin tubular conduit 19 is attached to the cap 13 by means of a fitting 16 which has a central bore 17 and a tubular extension 18 to snugly fit in the small hole on the cap. One end of the thin tubular conduit 19 is inserted into the tubular extension 18 to attach it to the cap. Other end of the thin tube 19 is open. The external diameter of the thin tube 19 is about 4 mm and the bore 20 is about 2 mm in diameter. The fitting 16 has a frustum conical shaped upper part with a central bore 17 and a tubular extension 18 and is made of flexible nontoxic material While a preferred embodiment of the apparatus for nasal passage rinsing is described in the foregoing, it will be understood that various modifications may be made without departing from the spirit and scope of the invention. Accordingly, other embodiments are within the scope of the claims.

I claim:

1. A method for rinsing nasal passages, comprising:
  (i) preparing an iodine-free saline solution by mixing measured amount of common salt with measured amount of warm water in a portable apparatus for gravity fed delivery of non-pressurized saline solution, the portable apparatus including a cap having an open cylindrical lower portion and a flat upper portion with a centrally located external tapering hollow nozzle, a hollow removable hollow conical frustum shaped and contoured dispenser tip, a flexible tube connecting said tapering hollow nozzle and said dispenser tip, a container for preparing and holding saline solution, the container having sidewalls and an axially aligned neck having an open end, wherein the lower portion of said cap and the neck of said container are configured to join together with a liquid tight connection, and a frustum conical shaped fitting protruding from fitting on said cap with a central bore of approximately 2 mm in diameter connected to a thin tubular conduit extending into the container terminating close to the bottom of the container, (ii) inserting a hollow conical frustum shaped and contoured dispenser tip into a nostril, (iii) closing the central bore of the frustum conical shaped fitting by applying pressure with a fingertip to prevent air from entering the container, (iv) elevating the portable apparatus above the user's nasal cavity, and (v) varying the fingertip pressure applied to the central bore to regulate the flow of air into the container and liquid into the nasal passages and varying the elevation of the apparatus to perform a nasal rinse with a controlled flow rate.

2. The method of claim 1, wherein continuous and steady flow of saline solution is dispensed into a nasal passage without applying pressure; and multiple removable dispenser tips, with upper parts having external diameters ranging from 9 to 15 mm configured to provide a seal against human nostril to minimize leaks at the nostril.

3. The method of claim 1, wherein the open cylindrically shaped lower portion of the cap has internal threads which are used to secure it to the external threads of the neck of said container to provide a liquid tight connection.

4. The method of claim 1, wherein said removable contoured dispenser tip has an open conical frustum shaped lower portion with a lip, a closed upper end with a centrally located hole, rounded upper edges and tapering sides, external diameters of 9 to 15 mm at the upper end, and is attached to said flexible tube using a snug fit connection.

5. The method of claim 1, wherein said flexible tube is at least 160 mm long and has an external diameter of about 9 mm and an internal diameter of about 6 mm.

6. The apparatus of claim 1, wherein said thin tubular conduit lets airflow into said container, when held inverted, allowing a continuous and steady fluid flow from said container and precludes liquid flow through it as its free end is always above liquid surface.

7. The method of claim 1, wherein said container is made of nontoxic material.

8. The method of claim 1, wherein said fitting has a conical frustum shaped upper portion with a central bore and a hollow cylindrical lower portion and allows to control outside air flow into said container is attached to said cap using a snug fit connection.

* * * * *